US012496260B1

(12) United States Patent
Lou et al.

(10) Patent No.: US 12,496,260 B1
(45) Date of Patent: Dec. 16, 2025

(54) LIQUID EYELINER PEN

(71) Applicant: JOTIM DAILY CHEMICAL (HANGZHOU) COMPANY LTD., Zhejiang (CN)

(72) Inventors: Biao Lou, Zhejiang (CN); Liyu Chen, Zhejiang (CN)

(73) Assignee: JOTIM DAILY CHEMICAL (HANGZHOU) COMPANY LTD., Zhejiang (CN)

( * ) Notice: Subject to any disclaimer, the term of this patent is extended or adjusted under 35 U.S.C. 154(b) by 0 days.

(21) Appl. No.: 19/234,524

(22) Filed: Jun. 11, 2025

(30) Foreign Application Priority Data

Feb. 19, 2025 (CN) ........................ 202520279773.1

(51) Int. Cl.
*A61K 8/02* (2006.01)
*A45D 34/04* (2006.01)
*B01F 33/25* (2022.01)

(52) U.S. Cl.
CPC .......... *A61K 8/0229* (2013.01); *A45D 34/042* (2013.01); *A61K 2800/87* (2013.01); *B01F 33/25* (2022.01); *B01F 33/251* (2022.01); *B01F 33/254* (2022.01)

(58) Field of Classification Search
CPC .. A61K 8/0229; A61K 2800/87; A45D 34/04; A45D 34/042; A45D 34/048; A45D 40/26; A45D 40/262; B01F 33/251; B01F 33/25; B01F 33/254
USPC ...................... 401/4, 198, 199; 366/129, 130
See application file for complete search history.

(56) References Cited

U.S. PATENT DOCUMENTS

| | | | | | |
|---|---|---|---|---|---|
| 2,983,946 | A * | 5/1961 | Edelstone | A45D 34/045 401/229 |
| 3,136,532 | A * | 6/1964 | Rudnick | B01F 33/5011 366/130 |
| 9,295,316 | B2 * | 3/2016 | Mathiez | A45D 34/048 |
| 10,327,530 | B2 * | 6/2019 | Tarling | A45D 34/045 |
| 2002/0110403 | A1 * | 8/2002 | Nishitani | B43K 8/03 401/196 |
| 2012/0266907 | A1 * | 10/2012 | Chan | A45D 34/042 132/218 |

FOREIGN PATENT DOCUMENTS

CN 212307114 U 1/2021

* cited by examiner

*Primary Examiner* — David J Walczak
(74) *Attorney, Agent, or Firm* — Cooper Legal Group, LLC

(57) ABSTRACT

A liquid eyeliner pen includes a barrel, an accommodating cavity is formed in the barrel, the barrel is connected with a liquid delivery assembly, an end of the liquid delivery assembly is in communication with the accommodating cavity, the barrel is connected with a cap configured for covering the liquid delivery assembly, a stirring element with a stirring end is slidably connected in the accommodating cavity, and the stirring end is located at a dead corner.

6 Claims, 14 Drawing Sheets

LIQUID EYELINER PEN

CROSS-REFERENCE TO RELATED APPLICATION

This application claims the priority to Chinese patent application serial no. 202520279773.1, filed on Feb. 19, 2025. The entirety of Chinese patent application serial no. 202520279773.1 is hereby incorporated by reference herein and made a part of this specification.

TECHNICAL FIELD

The present application relates to the technical field of liquid eyeliner pens, and in particular, to a liquid eyeliner pen.

BACKGROUND ART

A liquid eyeliner pen is a cosmetic tool for defining eye contours, which combines the precise lines of liquid eyeliners with the convenient application of eyeliner pencils, thereby serving as a highly favored eye makeup product in modern cosmetics.

Existing Chinese Patent Publication No. CN212307114U discloses an antibacterial and antistatic liquid eyeliner pen. A spring is disposed at an inner bottom of an outer cap of the liquid eyeliner pen. One end of the spring is fixed at the inner bottom of the outer cap, and the other end of the spring is fixed at an outer circumference of a bottom of an inner cap. An inner circumference of a cap opening of the inner cap abuts against the tapered surface of the barrel at the cap opening so as to interlock with it. A brush seat, a distribution block, a liquid wick, and a steel ball are disposed in the barrel. A base of a brush is fixed to the brush seat. The brush seat abuts against an internal shoulder ring on an inner circumference of a bore in the barrel, and bristles of the brush extend out of the brush seat and the bore of the barrel. A plug is disposed at an end bore of the barrel. Snap fit positioning ribs on the plug are engaged with recessed snap guide ribs of the barrel. The steel ball is located in an internal chamber between the plug and the distribution block in the barrel. Key features of the structural design of the liquid eyeliner pen are as follows. The liquid wick is disposed at a central axis of the distribution block in the barrel. A wick tip of the liquid wick is inserted into the base of the brush and abuts against the brush. An upper snap fit recess and a lower snap fit recess are respectively defined at two ends of an outer circumference of the distribution block. The upper snap fit recess and the lower snap fit recess of the distribution block are respectively engaged with an inner transition ring and an inner conical rib on an inner wall of the barrel. Wick blades are provided on the outer circumference of the distribution block between the upper snap fit recess and the lower snap fit recess. An end of the distribution block is inserted into an inner conical cavity of the bore in the barrel. The inner transition ring of the barrel is located along the inner circumference of the conical bore of the barrel. An outer shoulder ring is disposed on the outer circumference of the barrel corresponding to the inner transition ring. The barrel is configured as an antibacterial and antistatic barrel.

The foregoing antibacterial and antistatic liquid eyeliner pen is convenient to use, has a long service life, offers excellent ergonomic feel during use, possesses superior sealing performance and stability, and is suitable for automated production and assembly. It is suitable for use as a substitute for conventional liquid eyeliner pens and allows structural optimizations in analogous products. However, the foregoing antibacterial and antistatic liquid eyeliner pen has some disadvantages. For example, a dead corner exists between the barrel and the distribution block. The steel ball cannot move to the dead corner when the liquid eyeliner pen is agitated. As a result, pigments and thickeners in an eyeliner liquid tend to accumulate in the dead corner, leading to nonuniform eyeliner liquid mixing and liquid discharge, which compromises user experience and necessitates further improvements.

SUMMARY

An objective of the present application is to provide a liquid eyeliner pen, which may improve the mixing effect of an eyeliner liquid.

A liquid eyeliner pen provided in the present application includes a barrel, an accommodating cavity is formed in the barrel, the barrel is connected with a liquid delivery assembly, an end of the liquid delivery assembly is in communication with the accommodating cavity, the barrel is connected with a cap configured for covering the liquid delivery assembly, a stirring element with a stirring end is slidably connected in the accommodating cavity, and the stirring end is located at a dead corner.

In the foregoing technical solution, before the liquid eyeliner pen is used, the barrel is agitated to move the stirring element in a length direction of the barrel. The stirring element stirs eyeliner liquid in the accommodating cavity in a movement process, and the stirring end of the stirring element may move to the dead corner to impact pigments that accumulate in the dead corner, such that the pigments may leave the dead corner and mix with the eyeliner liquid. In this way, the accumulation of pigments in the dead corner may be reduced, thereby improving the mixing effect of the eyeliner liquid.

Optionally, the stirring element is configured as a spring, and the stirring end is an end of the spring.

The spring is inexpensive, thereby reducing the costs. The spring is compressed to deform while maintaining a tendency to elastically reset, and in a movement process, the spring abuts against an inner wall of the accommodating cavity, thereby absorbing impact forces to protect the barrel.

Optionally, a ball is slidably connected in the accommodating cavity, and the spring abuts against the ball.

When the foregoing technical solution is adopted, the spring is compressed to deform while maintaining a tendency to elastically reset. The spring abuts against the ball to move the ball, thereby enhancing the impact of the ball on the eyeliner liquid, i.e., improving the mixing effect of the eyeliner liquid. The ball applies a force to the spring in a movement process, thereby improving the effect of impacting pigments in the dead corner by the stirring end.

Optionally, a ball is slidably connected in the accommodating cavity, and the spring surrounds the ball.

When the foregoing technical solution is adopted, the ball may move inward the spring in a movement process, which increases the movement path of the ball, i.e., increase the contact area between the ball and the eyeliner liquid, thereby improving the mixing effect of the eyeliner liquid.

Optionally, the end of the spring is configured as a bent end, and the bent end is bent toward an axial line of the spring.

When the foregoing technical solution is adopted, in a mounted state of the spring, the bent end is located at an end of the spring close to the liquid delivery assembly, and in a movement process of the spring, the bent end stirs the eyeliner liquid close to the liquid delivery assembly, a contact area with the eyeliner liquid is increased by the bent end, thereby improving the mixing effect of the liquid eyeliner there.

Optionally, two ends of the spring are both configured as bent ends.

When the foregoing technical solution is adopted, when the spring is mounted, it is not necessary to identify which end of the spring is configured with a bent end, thereby improving the mounting efficiency of the spring. Both ends are configured as bent ends to increase the contact area between the spring and the eyeliner liquid, thereby improving the mixing effect of the liquid eyeliner.

Optionally, the end of the spring is configured as a helical end, and a pitch of the helical end decreases stepwise.

When the foregoing technical solution is adopted, the contact area between the spring and the eyeliner liquid is increased through the helical end, thereby improving the mixing effect of the eyeliner liquid.

Optionally, the stirring element is a sleeve configured with a plurality of through holes, and the stirring end is an end of the sleeve.

When the foregoing technical solution is adopted, the end of the sleeve can impact the dead corner in a movement process of the sleeve, such that pigments leave the dead corner and mix with the eyeliner liquid. In this way, the accumulation of pigments in the dead corner can be reduced, thereby improving the mixing effect of the eyeliner liquid. The through holes guide the flow of the eyeliner liquid in the movement process of the sleeve, so that a flow path of the eyeliner liquid is increased, thereby improving the mixing effect of the eyeliner liquid.

Optionally, a ball is slidably connected in the accommodating cavity, and the sleeve surrounds the ball.

When the foregoing technical solution is adopted, the ball rolls in the sleeve, which increases a contact area between the ball and the eyeliner liquid, thereby improving the mixing effect of the eyeliner liquid.

Optionally, the end of the sleeve away from the liquid delivery assembly is formed with a guide ring surface, a radius of the guide ring surface decreases toward the liquid delivery assembly, and the guide ring surface is configured for abutting against the ball.

When the foregoing technical solution is adopted, the guide ring surface guides the rolling of the ball, thereby enabling the ball to smoothly roll into the sleeve.

In summary, the present application includes at least one of the following beneficial technical effects:

1. The stirring element stirs the eyeliner liquid in the accommodating cavity in a movement process, and the stirring end of the stirring element can move to the dead corner to impact pigments that accumulate in the dead corner, enabling the pigments to leave the dead corner and mix with the eyeliner liquid, thereby improving the mixing effect of the eyeliner liquid.

2. In the mounted state of the spring, the bent end is located at an end of the spring close to the liquid delivery assembly, and in the movement process of the spring, the bent end stirs the eyeliner liquid close to the liquid delivery assembly, by which the contact area between the spring and the eyeliner liquid is increased by the bent end, thereby improving the mixing effect of the eyeliner liquid there.

DETAILED DESCRIPTION

The present application is further described below in detail with reference to FIG. 1 to FIG. 14.

The present application discloses a liquid eyeliner pen.

Figure 1:
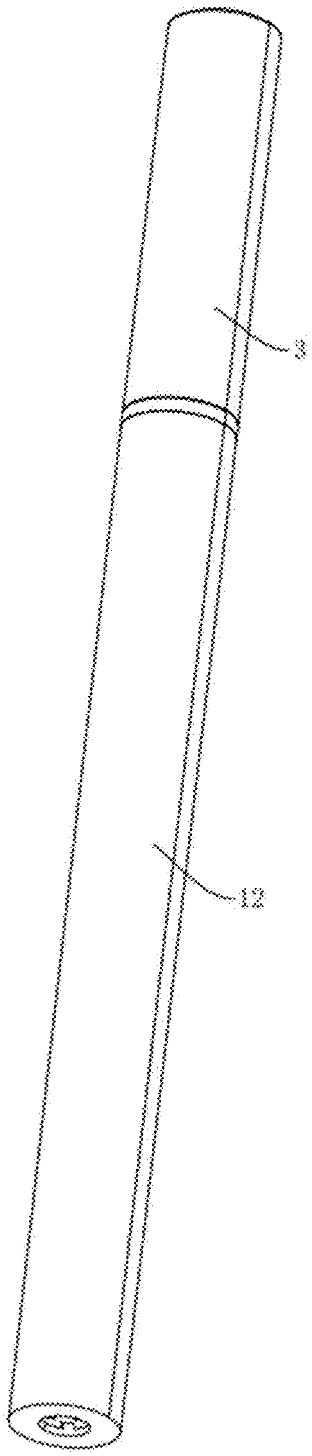
FIG. 1 is an overall schematic structural diagram according to Embodiment 1 of the present application.
Figure 2:
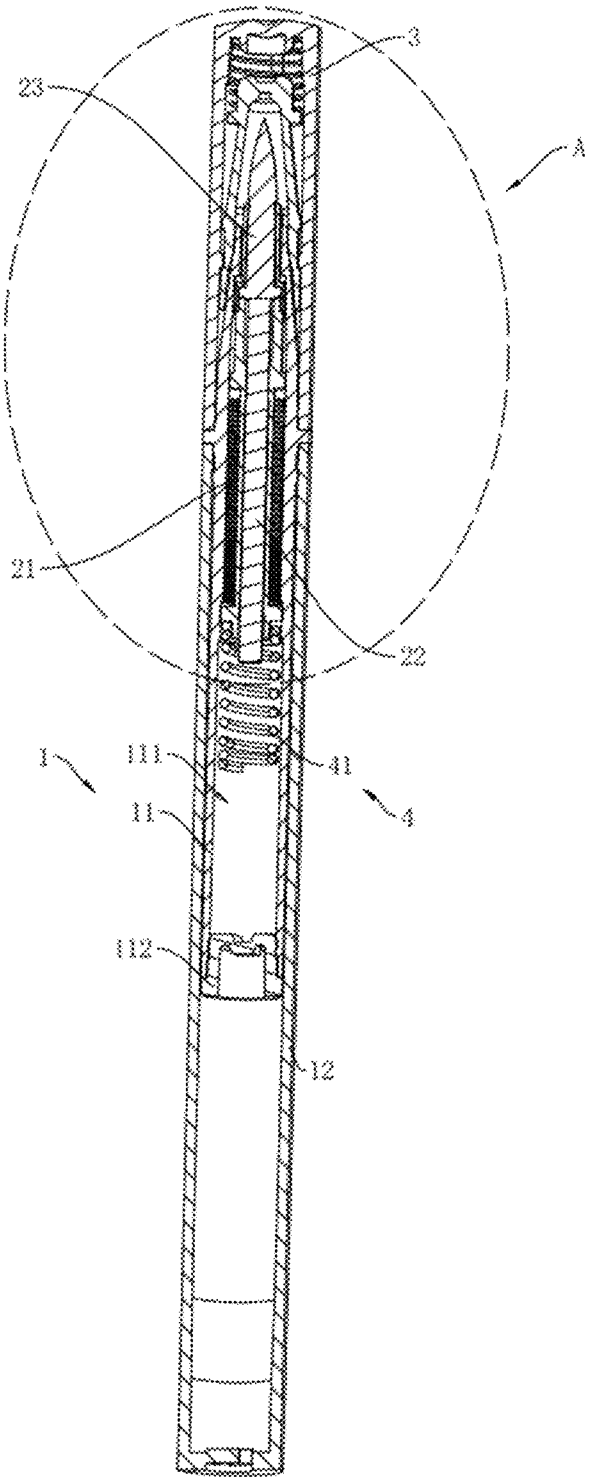
FIG. 2 is a cross-sectional view of FIG. 1.
Figure 3:
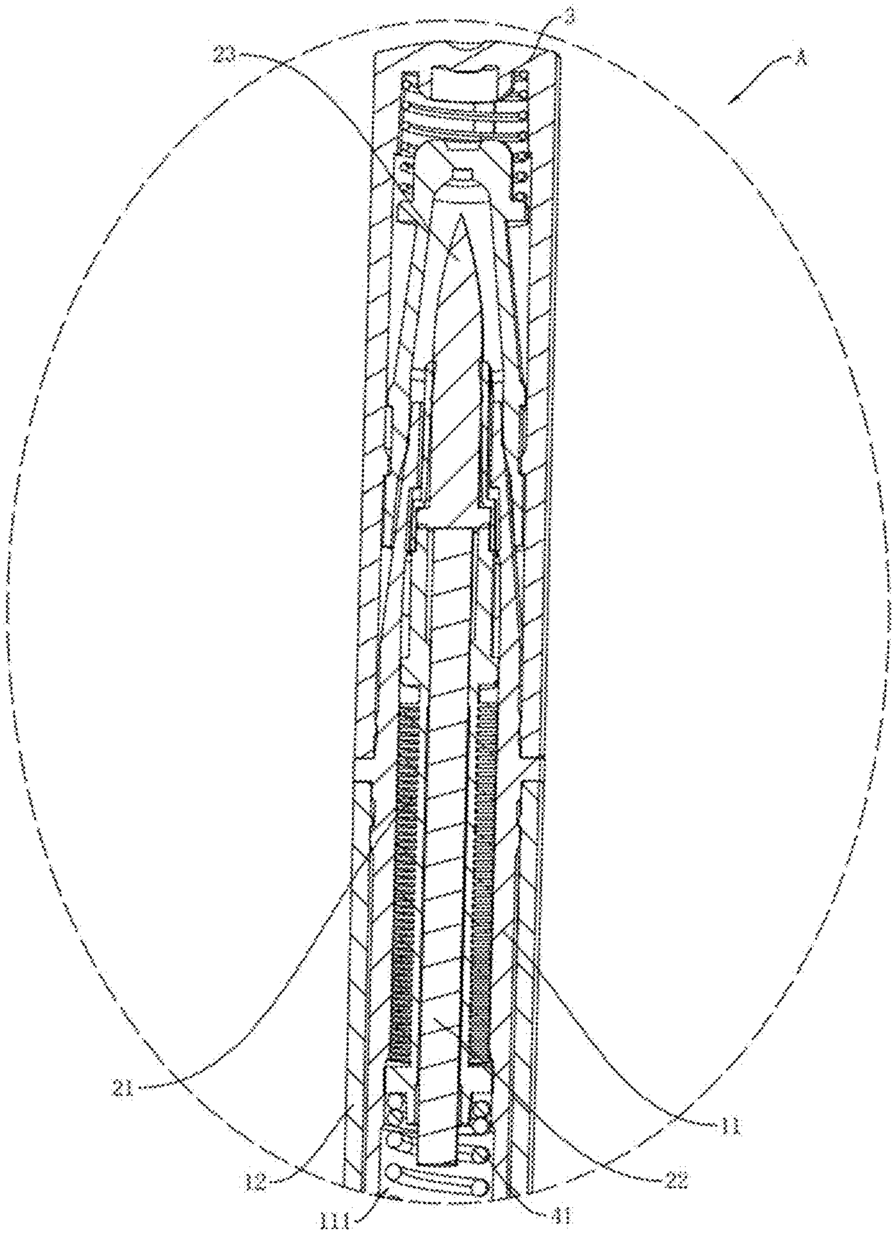
FIG. 3 is an enlarged view of portion A in FIG. 2.
Figure 4:
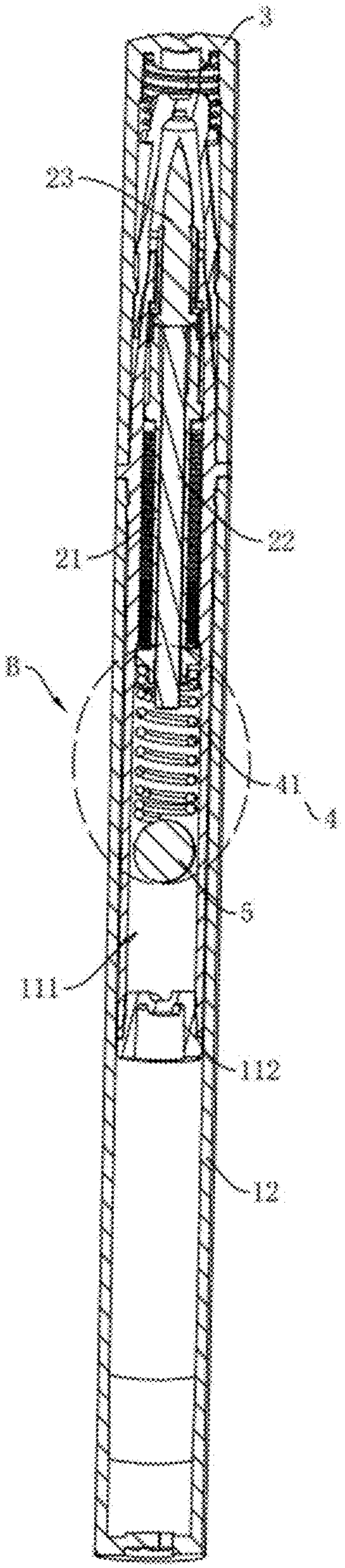
FIG. 4 is a cross-sectional view according to Embodiment 2 of the present application, showing a ball.
Figure 5:
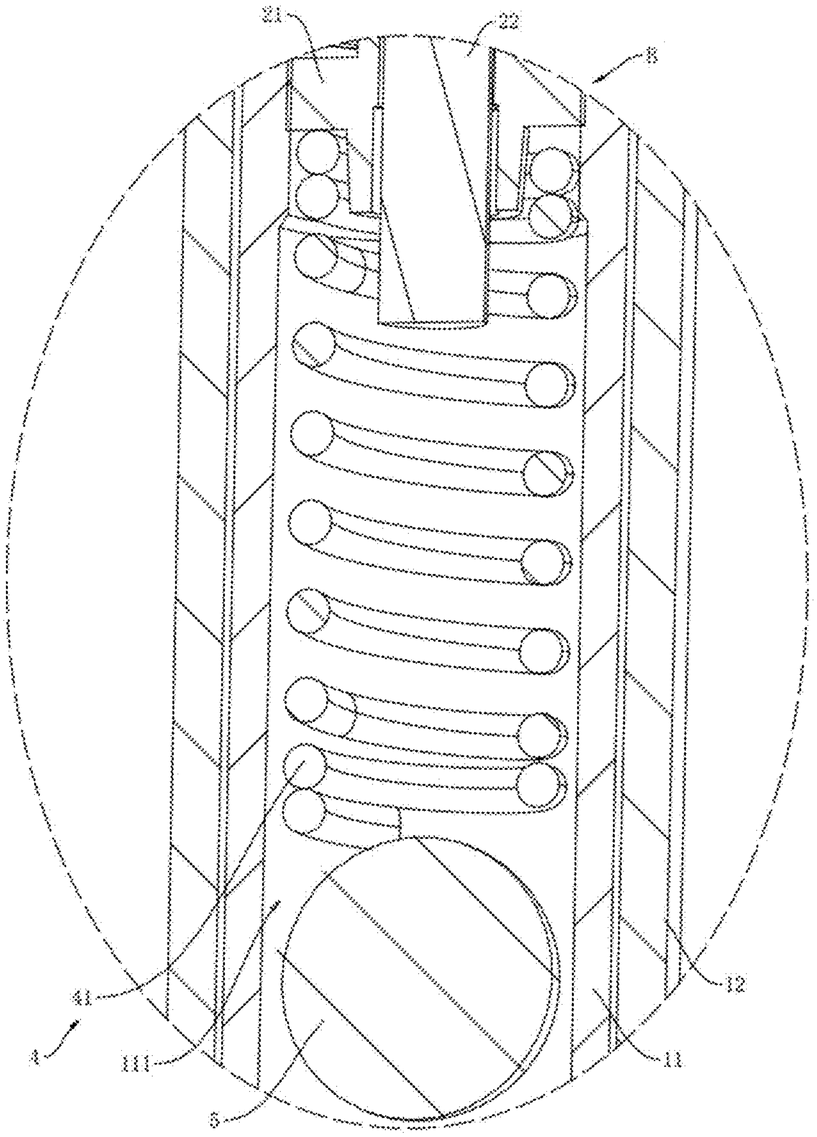
FIG. 5 is an enlarged view of portion B in FIG. 4.
Figure 6:
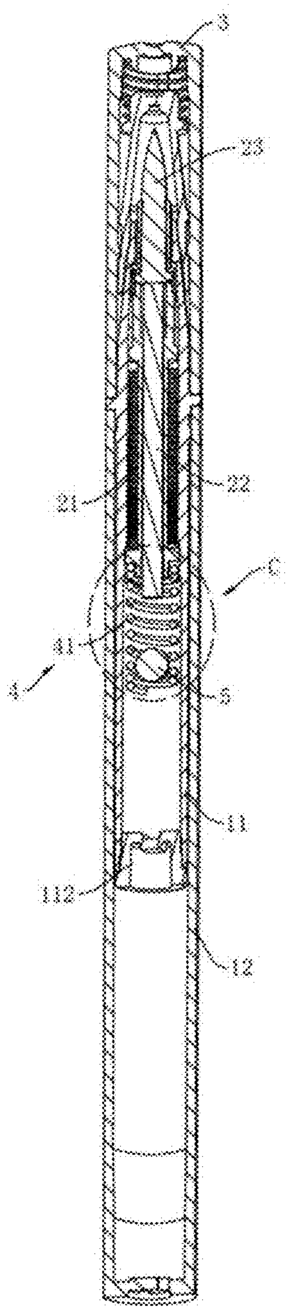
FIG. 6 is another cross-sectional view according to Embodiment 2 of the present application, showing the ball.
Figure 7:
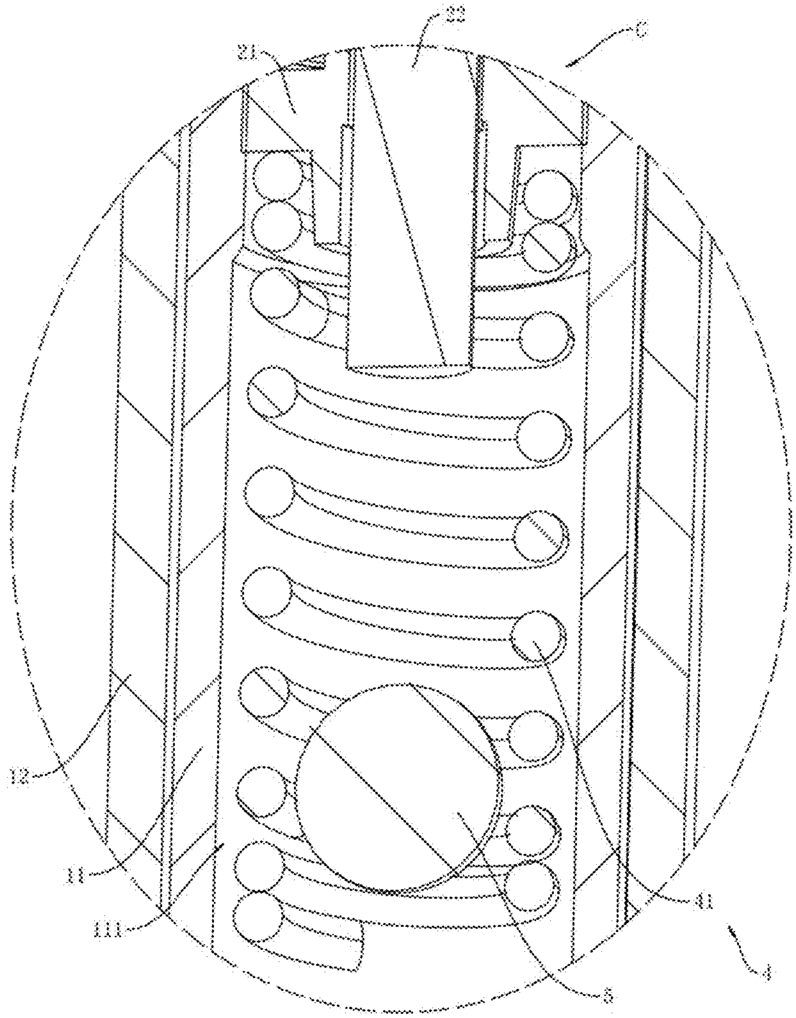
FIG. 7 is an enlarged view of portion C in FIG. 6.
Figure 8:
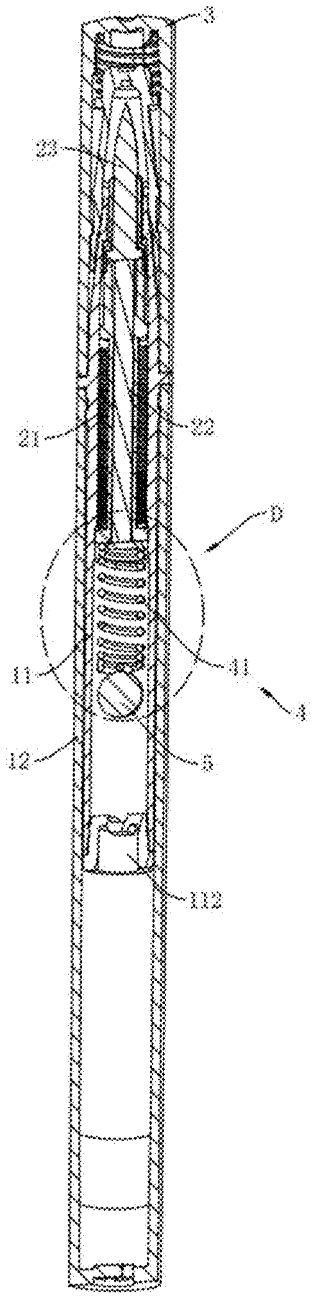
FIG. 8 is a cross-sectional view according to Embodiment 3 of the present application.
Figure 9:
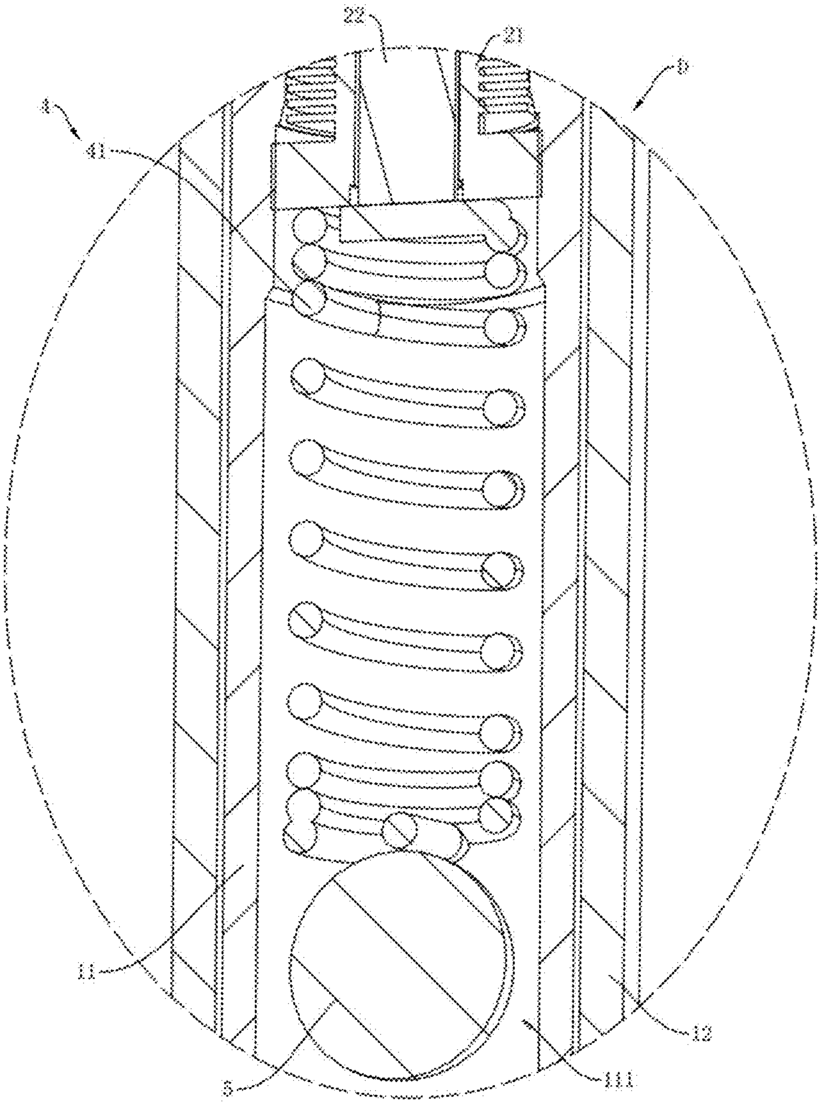
FIG. 9 is an enlarged view of portion D in FIG. 8.
Figure 10:
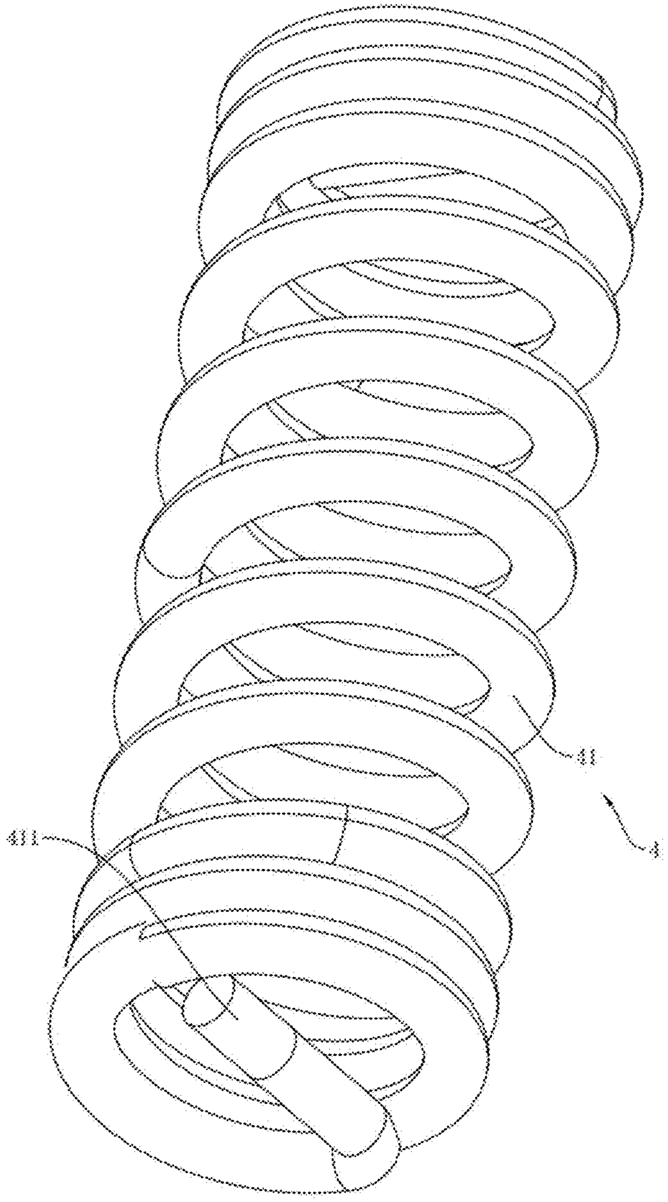
FIG. 10 is an overall schematic structural diagram of a spring, showing a bent end.
Figure 11:
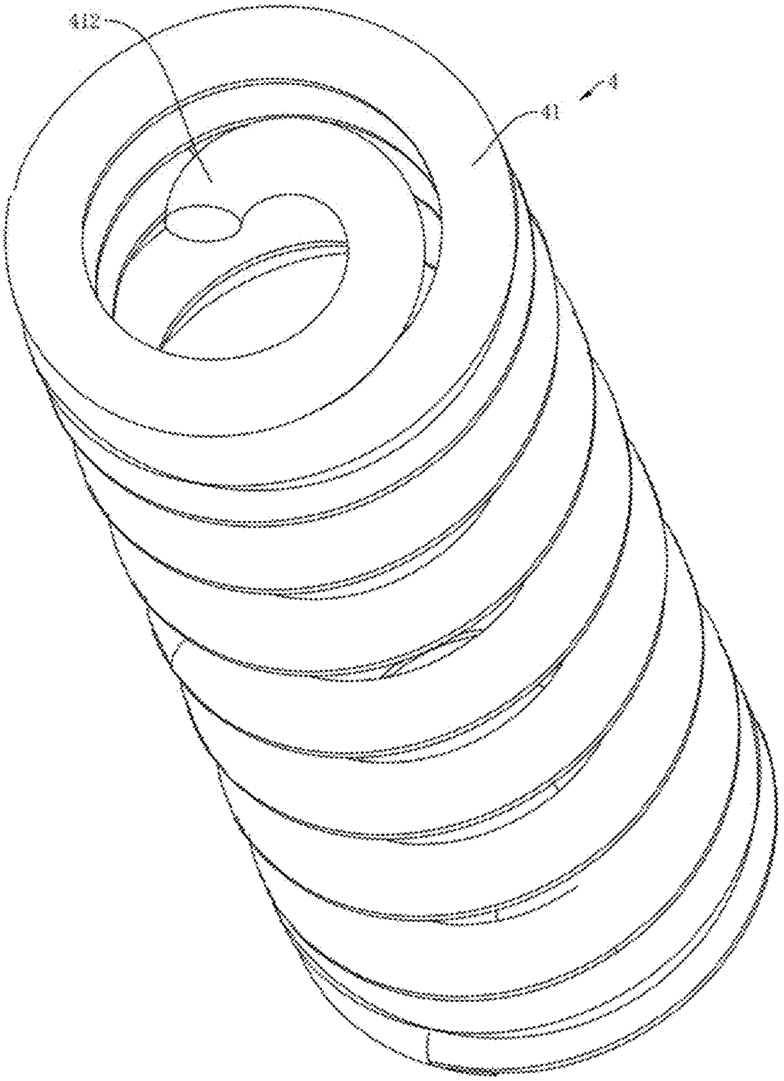
FIG. 11 is another overall schematic structural diagram 2 of a spring, showing a helical end.

Referring to FIG. 1, FIG. 2, and FIG. 3, the liquid eyeliner pen includes a barrel 1. The barrel 1 includes an inner tube 11 and an outer tube 12. The inner tube 11 is fixedly connected to the outer tube 12. An accommodating cavity 111 is formed in the inner tube 11. One end of the inner tube 11 is fixedly connected with an inner stopper 112 which is used for sealing the accommodating cavity 111, and the other end of the inner tube 11 is connected with a liquid delivery assembly. The liquid delivery assembly includes a distribution block 21 fixedly connected in the inner tube 11, a liquid wick 22 fixedly connected in the distribution block 21, and a brush head 23 fixedly connected to the liquid wick 22. The brush head 23 is located at an end of the liquid wick 22 away from the inner stopper 112. The inner tube 11 is connected with a cap 3 for covering the brush head 23. The inner tube 11 snaps into the cap 3.

Referring to FIG. 2 and FIG. 3, in this embodiment, an end of the liquid wick 22 away from the brush head 23 protrudes from the distribution block 21, so that a dead corner is formed between the distribution block 21 and the inner tube 11. A stirring element 4 is slidably connected in the accommodating cavity 111. The stirring element 4 is provided with a stirring end, which may move to the dead corner in a movement process of the stirring element 4. The stirring element 4 is a spring 41, and the stirring end is an end of the spring 41.

The implementation principle of the liquid eyeliner pen in this embodiment is as follows.

Before the liquid eyeliner pen is used, the barrel 1 is agitated to move the spring 41 in a length direction of the barrel 1. The spring 41 stirs eyeliner liquid in the accommodating cavity 111 in a movement process, and the stirring end of the spring 41 may move to the dead corner to impact pigments that accumulate in the dead corner, such that the pigments may leave the dead corner and mix with the eyeliner liquid. In this way, the accumulation of pigments in the dead corner may be reduced, thereby improving the mixing effect of the eyeliner liquid.

Embodiment 2

Referring to FIG. 4, FIG. 5, FIG. 6, and FIG. 7, this embodiment differs from Embodiment 1 in that a ball 5 is slidably connected in the accommodating cavity 111. When the diameter of the ball 5 is greater than the inner diameter of the spring 41, the spring 41 is located between the ball 5 and the distribution block 21. When the diameter of the ball 5 is less than the inner diameter of the spring 41, the ball 5 is movable in the spring 41.

Embodiment 3

Referring to FIG. 8, FIG. 9, FIG. 10, and FIG. 11, this embodiment differs from Embodiment 1 in that the end of the liquid wick 22 away from the brush head 23 is flush with an end of the distribution block 21 away from the brush head 23. Two ends of the spring 41 are both configured as bent ends 411. Each of the bent ends 411 is straight-formed. The bent end 411 is bent toward an axial line of the spring 41. In other embodiments, the two ends of the spring 41 are both configured as helical ends 412, and a pitch of each of the helical ends 412 decreases stepwise.

Embodiment 4

Figure 12:
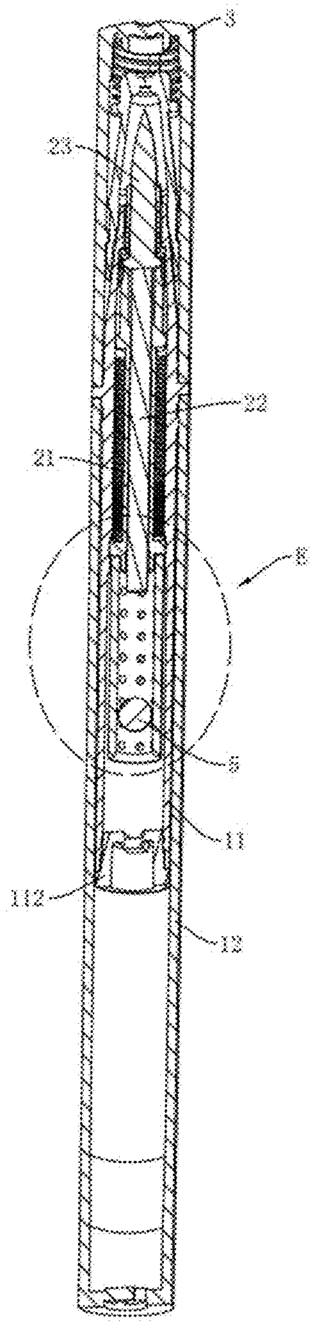
FIG. 12 is a cross-sectional view according to Embodiment 4 of the present application.
Figure 13:
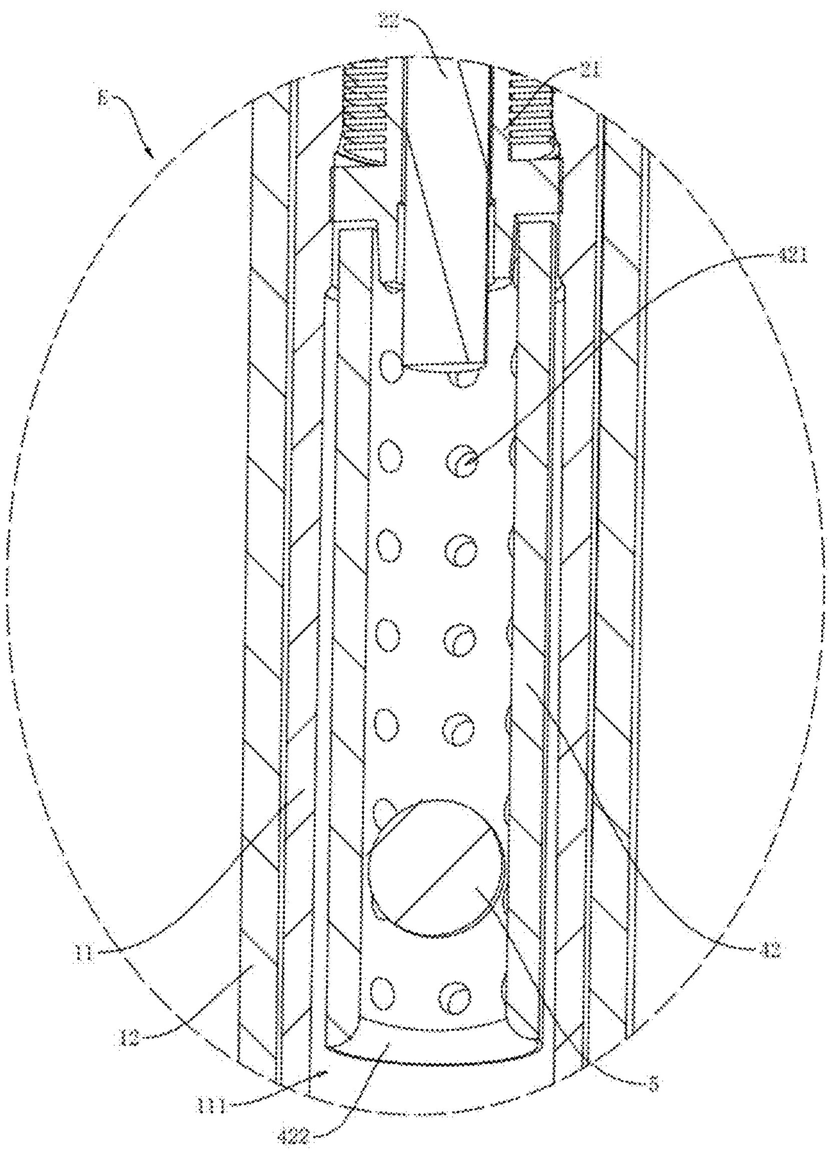
FIG. 13 is an enlarged view of portion E in FIG. 12.
Figure 14:
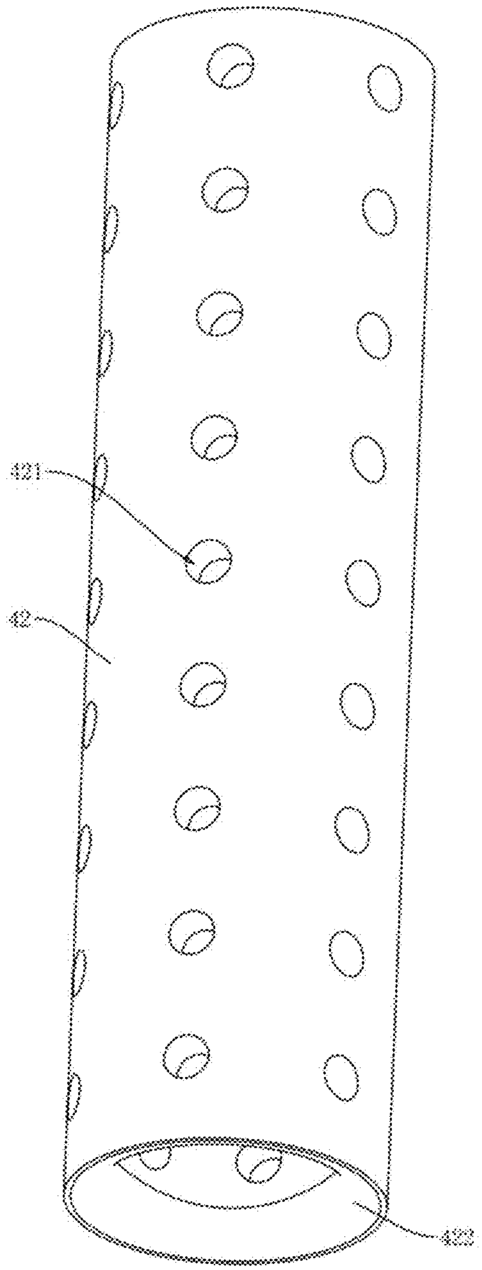
FIG. 14 is an overall schematic structural diagram of a sleeve.

Referring to FIG. 12, FIG. 13, and FIG. 14, this embodiment differs from Embodiment 1 in that the stirring element 4 is a sleeve 42. A plurality of through holes 421 are formed in an outer surface of the sleeve 42. The stirring end is an end of the sleeve 42. The sleeve 42 is formed with a guide ring surface 422. The guide ring surface 422 is located at an end of the sleeve 42 away from the liquid delivery assembly. The radius of the guide ring surface 422 decreases stepwise toward the liquid delivery assembly. The ball 5 is slidably connected in the accommodating cavity 111, and the diameter of the ball 5 is less than the inner diameter dimension of the sleeve 42.

Optional embodiments of the present application are provided above, but are not used to limit the scope of protection of the present application. Therefore, all equivalent changes made according to the structure, shape, and principle of the present application shall fall within the scope of protection of the present application.

LIST OF REFERENCE SIGNS

1 barrel
11 inner tube
111 accommodating cavity
112 inner stopper
12 outer tube
21 distribution block
22 liquid wick
23 brush head
3 cap
4 stirring element
41 spring
411 bent end
412 helical end
42 sleeve
421 through hole
422 guide ring surface
5 ball

What is claimed is:

1. A liquid eyeliner pen, comprising a barrel, wherein an accommodating cavity is formed in the barrel, the barrel is connected with a liquid delivery assembly, an end of the liquid delivery assembly is in communication with the accommodating cavity, the barrel is connected with a cap configured for covering the liquid delivery assembly, a stirring element with a stirring end is slidably connected in the accommodating cavity, the stirring end is located at a dead corner, the barrel comprises an inner tube and an outer tube, the accommodating cavity is formed in the inner tube, the liquid delivery assembly comprises a distribution block fixedly connected in the inner tube, and the dead corner is formed between the distribution block and the inner tube, wherein the stirring element is configured as a spring, and the stirring end is an end of the spring, and wherein a ball is slidably connected in the accommodating cavity, and the spring surrounds the ball.

2. The liquid eyeliner pen according to claim 1, wherein the end of the spring is configured as a bent end, and the bent end is bent toward an axial line of the spring.

3. The liquid eyeliner pen according to claim 1, wherein the end of the spring and a second end of the spring are both configured as bent ends.

4. The liquid eyeliner pen according to claim 1, wherein the end of the spring is configured as a helical end, and a pitch of the helical end decreases stepwise.

5. A liquid eyeliner pen, comprising a barrel, wherein an accommodating cavity is formed in the barrel, the barrel is connected with a liquid delivery assembly, an end of the liquid delivery assembly is in communication with the accommodating cavity, the barrel is connected with a cap configured for covering the liquid delivery assembly, a stirring element with a stirring end is slidably connected in the accommodating cavity, and the stirring end is located at a dead corner, the barrel comprises an inner tube and an outer tube, the accommodating cavity is formed in the inner tube, the liquid delivery assembly comprises a distribution block fixedly connected in the inner tube, and the dead corner is formed between the distribution block and the inner tube, wherein the stirring element is a sleeve configured with a plurality of through holes, and the stirring end is an end of the sleeve, and wherein a ball is slidably connected in the accommodating cavity, and the sleeve surrounds the ball.

6. The liquid eyeliner pen according to claim 5, wherein an end of the sleeve away from the liquid delivery assembly is formed with a guide ring surface, a radius of the guide ring surface decreases toward the liquid delivery assembly, and the guide ring surface is configured for abutting against the ball.

* * * * *